United States Patent
Sirch et al.

(10) Patent No.: US 7,112,707 B2
(45) Date of Patent: Sep. 26, 2006

(54) METHOD FOR THE ISOLATION OF TRIMETHYLOLPROPANE FROM A REACTION MIXTURE

(75) Inventors: Tilman Sirch, Schifferstadt (DE); Gerd Kaibel, Lampertheim (DE); Alexander Wartini, Heidelberg (DE); Matthias Dernbach, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 287 days.

(21) Appl. No.: 10/497,522

(22) PCT Filed: Dec. 6, 2002

(86) PCT No.: PCT/EP02/13882

§ 371 (c)(1),
(2), (4) Date: Jun. 3, 2004

(87) PCT Pub. No.: WO03/048093

PCT Pub. Date: Jun. 12, 2003

(65) Prior Publication Data

US 2004/0267055 A1    Dec. 30, 2004

(30) Foreign Application Priority Data

Dec. 7, 2001 (DE) .................. 101 60 180

(51) Int. Cl.
  *C07C 29/80* (2006.01)
  *C07C 29/82* (2006.01)
  *C07C 29/84* (2006.01)
(52) U.S. Cl. .................................................. 568/854
(58) Field of Classification Search ................. 568/854
  See application file for complete search history.

(56) References Cited

U.S. PATENT DOCUMENTS 6,187,971 B1    2/2001    Kratz et al.
2002/0189926 A1    12/2002    Dembach et al.

FOREIGN PATENT DOCUMENTS

DE    199 63 435    7/2001
EP    1 013 631    6/2000
WO    WO 98/28253    7/1998

*Primary Examiner*—Elvis O. Price
(74) *Attorney, Agent, or Firm*—Novak Druce & Quigg LLP

(57) ABSTRACT

Trimethylolpropane is isolated from a reaction mixture which has been obtained by reaction of n-butyraldehyde with formaldehyde in the presence of a base and, if appropriate, hydrogenation of the resulting mixture by distilling the mixture by means of a dividing wall column or a distillation column with a precolumn or a distillation column with an after-column. The process has low capital costs and a low energy consumption and gives reduced formation of high-boiling by-products.

9 Claims, 2 Drawing Sheets

METHOD FOR THE ISOLATION OF TRIMETHYLOLPROPANE FROM A REACTION MIXTURE

The present invention relates to a process for isolating trimethylolpropane from a reaction mixture which is obtained by reaction of n-butyraldehyde with formaldehyde in the presence of a base and, if appropriate, subsequent hydrogenation.

Trimethylolpropane, hereinafter also referred to as TMP for short, is a trihydric alcohol which is used on a large scale for the production of surface coatings, polyurethanes and polyesters. TMP is prepared by aldol condensation of n-butyraldehyde with formaldehyde. A distinction is made between different variants depending on the way the process is carried out.

In the Cannizzaro process, butyraldehyde is reacted with formaldehyde in the presence of a stoichiometric amount of base. This initially forms 2,2-dimethylolbutanal which then reacts with a further molecule of formaldehyde in a cross-Cannizzaro reaction to form formic acid and trimethylolpropane. The disadvantage of this method is that one molar equivalent of formate is formed as coproduct. This has to be worked up and increases the consumption of formaldehyde.

The hydrogenation process represents a further development. In this, butyraldehyde is reacted with formaldehyde in the presence of a catalytic amount of a tertiary amine. The reaction stops at the 2,2-dimethylolbutanal stage, and this product is subsequently hydrogenated to give trimethylolpropane. No stoichiometric amounts of formates are formed and the solution obtained is easier to work up since smaller amounts of interfering by-products are formed. Such a process is described, for example, in WO 98/28253. To achieve virtually complete conversion of the starting materials into dimethylolbutanal in this process, unreacted or partially reacted starting materials are separated off from the reaction mixture and returned to the aldol reaction step; the residue is treated catalytically and/or thermally to convert monomethylolbutanal into dimethylolbutanal and ethylacrolein, and the latter can be separated off and returned to the aldol reaction step. The crude TMP obtained by the process is worked up by distillation in a customary manner.

DE 199 63 435 describes a process for the purification by distillation of crude TMP which is obtained by the hydrogenation process. In this purification by distillation, water, methanol, trialkylamine and/or trialkylammonium formate are firstly separated off by distillation and the residue obtained is heated to a temperature at which TMP is volatile and compounds having higher boiling points than TMP are at least partially decomposed. TMP and compounds having lower boiling points than TMP are separated off by distillation and the distillate obtained is distilled to separate off the more volatile compounds and obtain pure TMP. The TMP obtained can then be subjected to another purification by distillation.

However, this process has the disadvantage that both the low boilers and TMP have to be taken off at the top, thus resulting in a higher energy consumption. In addition, the distillation in successive columns, especially when residence times in the bottoms of the columns are long, results in formation of significant amounts of undesirable by-products which reduce the product yield. Thus, the removal of the compounds which are more volatile than TMP is associated with formation of further high boilers, even though the mixture to be fractionated is the product from the top of the preceding distillation. Although these high boilers can be recirculated and partially decomposed thermally, it is uneconomical to circulate a relatively large amount of high boilers in this way. Furthermore, the construction and operation of a plurality of columns is a significant cost factor.

It is an object of the present invention to provide a process for isolating trimethylolpropane from a reaction mixture, which process has low capital costs and a low energy consumption and gives TMP of high purity.

We have found that this object is achieved by a process in which i) the mixture is introduced into a feed column having an enrichment section located above the feed point and a stripping section located below the feed point, ii) a lower combining column which has a condenser at the upper end of the column and communicates with the upper end of the enrichment section and a second combining column which has a heater at the lower end of the column and communicates with the lower end of the stripping section are provided, iii) an offtake column which communicates with the upper combining column and the lower combining column is provided, iv) pure trimethylolpropane is taken off from the offtake column at a side offtake, and compounds having boiling points lower than that of trimethylolpropane are taken off at the top or in the upper region of the upper combining column and compounds which have boiling points higher than that of trimethylolpropane are taken off at the bottom or in the lower region of the lower combining column.

The process of the invention is suitable for the work-up of both reaction mixtures which are obtained by the Cannizzaro process, i.e. in the presence of a stoichiometric amount of base, and mixtures which are obtained by the hydrogenation process, i.e. in the presence of a catalytic amount of a tertiary amine with subsequent hydrogenation.

The feed column, offtake column, upper combining column and lower combining column can be discrete plant components or be sections or chambers of a column which combines a plurality of functions. The expression "communicating columns" means that an exchange of both ascending vapor and descending condensate occurs between them.

In a preferred embodiment, the distillation is carried out using a dividing wall column, i.e. the feed column and the offtake column are configured as chambers which are open to a combining zone at each end and extend over part of the longitudinal dimension of a column and are separated from one another by a dividing wall. Distillation columns having a dividing wall are known per se and are described, for example, in ECN, Oct. 2–8, 1995, p. 26, "BASF Distils Energy Savings"; Chem. Eng. Res. Des. (1993) 71(3), p. 307, "The control of dividing wall column"; U.S. Pat. No. 2,471,134, Chem. Eng. Res. Des., Part A: Trans IChemE, September 1993, pp. 639–644, "Heat transfer across the wall of dividing wall".

In alternative embodiments, the distillation is carried out using a distillation column having a thermally coupled precolumn, i.e. the offtake column, the upper combining column and the lower combining column are configured as a one-piece distillation column and the feed column is configured as a precolumn before the distillation column. Alternatively, use is made of a distillation column having a thermally coupled after-column, i.e. the feed column, the upper combining column and the lower combining column are configured as a one-piece distillation column and the offtake column is configured as an after-column connected to the distillation column. Distillation columns with auxiliary columns are known and are described, for example, in Chem. Eng. Res. Des., Part A: Trans IChemE, March 1992, pp. 118–132, "The design and optimization of fully thermally coupled distillation columns".

The particular advantage of the present process results, inter alia, from the pure TMP fraction being able to be taken off at the side offtake and no longer having to be driven off via the top. This enables considerable energy savings compared to known processes to be achieved while maintaining unchanged quality. Furthermore, a reduction in the residence time of desired product in the hot bottom of the column which can be achieved under conditions which are comparatively gentle on the product reduces the yield-reducing formation of undesirable by-products. DE 199 634 35 would not have made the process of the present invention obvious, since an important feature of the process taught there is that the residue obtained after removal of water, methanol, trialkylamine and/or trialkylammonium formate is heated to a temperature at which TMP is volatile and compounds which have boiling points higher than that of TMP are at least partially decomposed.

Reaction mixtures which can be worked up by the process of the present invention usually comprise TMP together with water, methanol, monohydric alcohols such as methylbutanol and polyhydric alcohols, e.g. diols such as ethylpropanediol, and also acetals of formaldehyde and methanol with TMP and ethers of monohydric alcohols and polyhydric alcohols, e.g. diols, and possibly also tertiary ammonium formates. A reaction mixture obtained by the hydrogenation process usually has the following composition: from 10 to 40% by weight of trimethylolpropane, from 0.5 to 5% by weight of methanol, from 1 to 6% by weight of monohydric alcohols, from 1 to 10% by weight of tertiary ammonium formates, from 0 to 5% by weight of diols, from 2 to 10% by weight of high boilers and from 50 to 80% by weight of water.

To prepare TMP by the hydrogenation process, butyraldehyde is generally reacted with from 2 to 8 mol, preferably from 2 to 3.5 mol, of formaldehyde. The tertiary amine is generally used in an amount of from 0.001 to 0.2 molar equivalents, preferably from 0.01 to 0.07 molar equivalents, based on butyraldehyde. Suitable amines are trialkylamines such as trimethylamine or triethylamine. The reaction is generally carried out at from 5 to 100° C., preferably from 15 to 80° C. The residence time is, depending on the temperature, generally set to from 0.25 to 12 hours. It is particularly advantageous to use the method described in WO 98/28253. The dimethylolbutanal-containing product obtained in the aldol condensation is then hydrogenated under customary conditions in the presence of hydrogen gas. Suitable hydrogenation catalysts are, in particular, copper-containing supported catalysts as are described, for example, in WO 95/32171. The hydrogenation is advantageously carried out continuously, e.g. in a reaction tube which contains a catalyst bed and through which the reaction solution is pumped over the catalyst bed in the downflow mode or the upflow mode.

It has been found to be useful to remove the major part of the water present from the reaction mixture before the latter is introduced into the feed column, preferably to a residual water content of less than 5% by weight, in particular less than 2% by weight. In the dewatering procedure, other low boilers such as methanol and tertiary amine or tertiary ammonium formate present in the reaction mixture may also be separated off. In this way, the subsequent distillation can be carried out at a low pressure without the vapor pressure of water interfering. The water is preferably removed by distillation and/or by depressurization. Customary evaporators and/or distillation columns are suitable for this purpose; the removal of water can be carried out in one or more stages. It can be carried out at a pressure of from 20 mbar to ambient pressure. If low pressures in the range from 20 to 100 mbar and apparatuses having a short residence time, e.g. thin film evaporators, falling film evaporators or helical tube evaporators, are used, the tertiary ammonium formate is generally distilled off together with the low boilers. At pressures of more than 100 mbar, a reaction of tertiary ammonium formate with TMP to form tertiary amine and TMP formate takes place in the evaporator or the bottom of the distillation column. The tertiary amine distills off together with the low boilers. It can be freed of the methanol and water which are separated off together with it by distillation and can be reused for the aldol condensation.

If the dewatering of the reaction mixture is carried out under conditions under which TMP formate is formed to a relatively large extent, it can be advantageous to subject the reaction mixture to a treatment in which the TMP formate is cleaved and TMP is recovered before the reaction mixture is introduced into the feed column. This can, for example, be achieved in a manner known per se by carrying out a transesterification with an alcohol other than TMP, in particular a $C_1$–$C_4$-alkanol, preferably methanol, to form the formate of this alcohol and TMP. The transesterification can be carried out thermally or in the presence of a basic catalyst. It can be carried out as described in EP-A 289 921 in the presence of catalytic amounts of alkali metal or alkaline earth metal alkoxides or as described in WO 97/17313 in the presence of a tertiary amine, preferably triethylamine. The transesterification is preferably carried out at from 150 to 250° C., in particular from 180 to 220° C. If a catalyst is used, it is generally employed in an amount of from 0.005 to 0.05 mol per mole of TMP formate. The reaction time is typically up to ten hours. To achieve an appropriate reaction time, it is possible to use a separate reactor or a residence vessel.

The reaction mixture, which may have been dewatered and may have been subjected to a transesterification, is then introduced for the purposes of purification by distillation into a feed column which communicates as described with upper and lower combining columns which in turn communicate with an offtake column. In the purification by distillation, compounds which have boiling points higher than that of trimethylolpropane (high boilers, in particular TMP acetals) and compounds which have boiling points lower than that of trimethylolpropane are separated off. If the reaction mixture has been subjected to dewatering, the major part of the low boilers have already been removed and the purification by distillation separates off essentially intermediate boilers, i.e. compounds which have boiling points between those of water and TMP.

The purification by distillation is usually carried out at a pressure in the range from 5 to 100 mbar, preferably from 5 to 50 mbar, in particular from 10 to 30 mbar. The reflux ratio is generally from 0 to 30, preferably from 0.2 to 1.

The feed column, the upper combining column, the lower combining column and the offtake column contain separation-active internals. The internals are preferably in the form of ordered packing, e.g. Sulzer Mellapak, Sulzer BX, Montz A1 or Montz A3 or Kuhni Rhombopak, or random beds of packing elements, e.g. Dixon rings, Raschig rings, High-Flow rings or Raschig Super rings.

The reaction mixture is preferably introduced approximately in the middle of the feed column. The pure trimethylolpropane is preferably taken off in gaseous or liquid form, preferably gaseous form, at a side offtake approximately in the middle of the offtake column. The pure TMP generally has a purity of at least 98.5% by weight and a color number of from 0 to 200 APHA (determined in accordance with DIN ISO 6271; ASTM-D 1209-93). A stream taken from the high boilers which collect at the bottom of the column is discharged to prevent accumulation of relatively high-boiling and/or color-imparting components. A steady-state TMP content of from 1 to 50% by weight is generally established in the bottom of the column. At the top, low and intermediate boilers having a TMP content of from 0 to 80% by weight are taken off.

The process of the present invention is illustrated by means of the accompanying figures and the following example.

Figure 1:
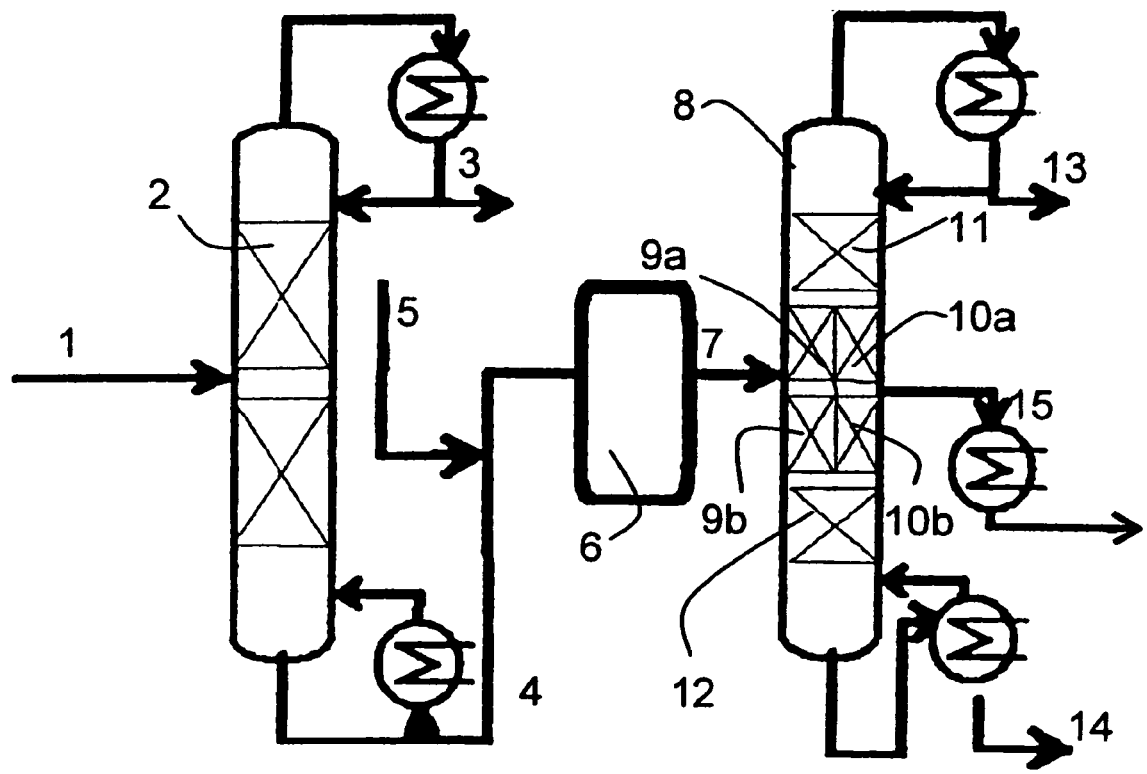
FIG. 1 shows a plant which is suitable for carrying out the process of the present invention and comprises a dividing wall column.

In the configuration shown in FIG. 1, the TMP-containing reaction mixture is introduced into the low boiler column 2 in which a mixture 3 of water and low boilers such as methanol or tertiary amine is separated off. The bottoms 4 taken from the low boiler column 2, which comprise TMP, high boilers and the low boilers which have not been separated off in the low boiler column 2, are fed into the reactor 6 in which the TMP formate is cleaved. This is achieved by addition of an alcohol, e.g. methanol, via line 5. The addition of the alcohol 5 and the use of the reactor 6 are optional. The treated reaction mixture 7 goes to the dividing wall column 8 which comprises a feed column 9 having an enrichment section 9a and a stripping section 9b, an offtake column 10 having a stripping section 10a and enrichment section 10b and also an upper combining column 11 and a lower combining column 12. Compounds 13 which have boiling points lower than that of TMP distill off at the top of the column 8. Bottoms 14 which are rich in high boilers remain. Pure TMP 15 is taken off at a side offtake on the offtake column.

Figure 2:
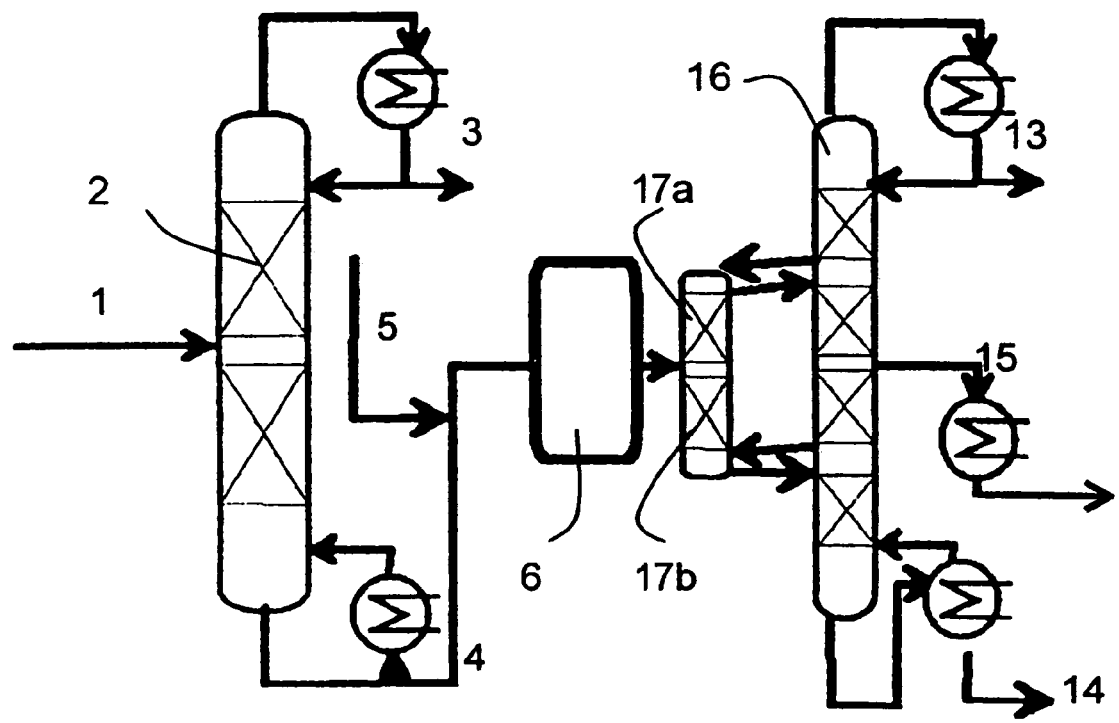
FIG. 2 shows a plant which is suitable for carrying out the process of the present invention and comprises a distillation column with upstream precolumn.

In FIG. 2, identical reference numerals have the same meanings as in FIG. 1. Unlike the plant shown in FIG. 1, a combination of a distillation column 16 and a thermally coupled precolumn 17 is used in place of the dividing wall column 8. The precolumn 17 has an enrichment section 17a and a stripping section 17b.

EXAMPLE

A reaction mixture which had been obtained by reaction of n-butyraldehyde with formaldehyde in the presence of trimethylamine and hydrogenation of the resulting mixture as described in Example 5 of WO 98/28253 and comprised 23.1% by weight of TMP, 0.4% by weight of methanol, 0.87% by weight of trimethylamine (as formate), 0.97% of weight of methylbutanol, 0.47% by weight of ethylpropanediol, 1.07% by weight of high boilers and 71.6% by weight of water was fed at a flowrate of 5 kg/hour into a low boiler column and dewatered at 400 mbar and a temperature of 175° C. at the bottom. The mixture was introduced in the middle of the column. Enrichment and stripping sections each comprised 1 m of sheet metal packing (nominal bore=50, Kühni Rhombopak 9M). The reflux ratio was 0.33. At the bottom of the column, 1.1 kg/hour of a stream comprising high boilers together with 80% by weight of TMP and about 1% by weight of water was taken off.

100 g/hour of the output from the column were fed into a dividing wall column (NB=100, upper combining section: 0.1 m of Dixon rings, lower combining section: 0.3 m of Dixon rings, dividing wall central, on the feed side 0.6 m of Dixon rings above the feed point and 0.4 m of Dixon rings below the feed point; on the offtake side 0.5 m of Dixon rings above the offtake point and 0.5 m of Dixon rings below the offtake point) for purification by distillation. The purification by distillation was carried out at a pressure at the top of 20 mbar, a reflux ratio of 0.5 and temperature-regulated discharge of the bottoms.

At the bottom of the column, high boilers having a residual TMP content of 12% by weight were separated off. The intermediate boilers, in particular 2-ethylpropanediol (5.5% by weight), having a residual TMP content of 66% by weight were taken off at the top. At the side offtake, TMP having a purity of 99.0% by weight and a color number of less than 30 APHA were taken off. The overall yield of the purification by distillation was 79% by weight.

We claim:

1. A process for isolating trimethylolpropane from a reaction mixture which has been obtained by reaction of n-butyraldehyde with formaldehyde in the presence of a base and, if appropriate, hydrogenation by distillation, wherein
   i) the mixture is introduced into a feed column having an enrichment section located above the feed point and a stripping section located below the feed point,
   ii) an upper combining column which has a condenser at the upper end of the column and communicates with the upper end of the enrichment section and a lower combining column which has a heater at the lower end of the column and communicates with the lower end of the stripping section are provided,
   iii) an offtake column which communicates with the upper combining column and the lower combining column is provided,
   iv) pure trimethylolpropane is taken off from the offtake column at a side offtake, and compounds having boiling points lower than that of trimethylolpropane are taken off at the top or in the upper region of the upper combining column and compounds which have boiling points higher than that of trimethylolpropane are taken off at the bottom or in the lower region of the lower combining column.

2. A process as claimed in claim 1, wherein the reaction mixture has been obtained by reaction of n-butyraldehyde with formaldehyde in the presence of a catalytic amount of a tertiary amine and subsequent hydrogenation.

3. A process as claimed in claim 1 or 2, wherein the major part of the water present is removed from the reaction mixture before this reaction mixture is introduced into the feed column.

4. A process as claimed in claim 3, wherein the dewatered reaction mixture is admixed with an alcohol other than trimethylolpropane before this reaction mixture is introduced into the feed column.

5. A process as claimed in any of the preceding claims, wherein the feed column and the offtake column are configured as chambers which are open to a combining zone at each end and extend over part of the longitudinal dimension of a column and are separated from one another by a dividing wall.

6. A process as claimed in any of claims 1 to 4, wherein the offtake column, the upper combining column and the lower combining column are configured as a one-piece distillation column and the feed column is configured as a thermally coupled precolumn before the distillation column.

7. A process as claimed in any of claims 1 to 4, wherein the feed column, the upper combining column and the lower combining column are configured as a one-piece distillation column and the offtake column is configured as a thermally coupled after-column connected to the distillation column.

8. A process as claimed in any of the preceding claims, wherein the feed column, the upper combining column, the lower combining column and the offtake column contain separation-active internals in the form of ordered packing and/or random beds of packing elements.

9. A process as claimed in any of the preceding claims, wherein the distillation is carried out at a pressure in the range from 5 to 100 mbar.

* * * * *

UNITED STATES PATENT AND TRADEMARK OFFICE
CERTIFICATE OF CORRECTION

PATENT NO. : 7,112,707 B2
APPLICATION NO. : 10/497522
DATED : September 26, 2006
INVENTOR(S) : Sirch et al.

It is certified that error appears in the above-identified patent and that said Letters Patent is hereby corrected as shown below:

In Claim 3, column 6, indicated line 49:
"claim 1 or 2" should read --claim 1--

In Claim 5, column 6, indicated line 57:
"any of the preceeding claims" should read --claim 1--

In Claim 6, column 6, indicated line 63:
"any of claims 1 to 4" should read --claim 1--

In Claim 7, column 7, indicated line 1:
"any of claims 1 to 4" should read --claim 1--

In Claim 8, column 7, indicated line 6:
"any of the preceeding claims" should read --claim 1--

In Claim 9, column 8, indicated line 3:
"any of the preceeding claims" should read --claim 1--

Signed and Sealed this

Thirteenth Day of February, 2007

JON W. DUDAS
*Director of the United States Patent and Trademark Office*